United States Patent [19]

Kaetsu et al.

[11] 4,193,845

[45] Mar. 18, 1980

[54] IMMOBILIZATION OF ENZYMES OR BACTERIAL CELLS

[75] Inventors: Isao Kaetsu; Hiroshi Watanabe, both of Takasaki; Tomotaro Sato, Sagamihara; Akihiko Ito, Takasaki, all of Japan

[73] Assignee: Japan Atomic Energy Research Institute, Tokyo, Japan

[21] Appl. No.: 688,081

[22] Filed: May 19, 1976

Related U.S. Application Data

[63] Continuation-in-part of Ser. No. 523,162, Nov. 12, 1974, abandoned.

[30] Foreign Application Priority Data

Nov. 15, 1973 [JP] Japan .............................. 48-127763

[51] Int. Cl.$^2$ .......................... C07G 7/02; C12K 1/00
[52] U.S. Cl. ......................................... 435/182; 260/8; 435/173
[58] Field of Search ............... 195/59, 63, 68, DIG. 4; 260/8; 204/159.16, 159.22

[56] References Cited

U.S. PATENT DOCUMENTS

| 3,859,169 | 1/1975 | O'Driscoll et al. | 195/63 |
| 3,860,490 | 1/1975 | Guttag | 195/59 X |
| 3,871,964 | 3/1975 | Huper et al. | 195/63 |
| 3,933,587 | 1/1976 | Maeda et al. | 195/68 |
| 3,962,038 | 6/1976 | Kamashima et al. | 195/68 |

*Primary Examiner*—David M. Naff
*Attorney, Agent, or Firm*—Browdy and Neimark

[57] ABSTRACT

This invention relates to polymer composition having fixed bacterial cells and/or fixed enzyme, in which the enzyme or cells are dispersed within the polymer. The polymer composition is prepared by mixing an aqueous enzyme solution or an aqueous dispersion of bacterial cells with one or more monomers selected from the group consisting of hydroxyethyl methacrylate, hydroxyethyl acrylate, hydroxypropyl methacrylate and hydroxypropyl acrylate and then polymerizing or co-polymerizing the monomer(s) contained in the mixture by means of ionizing radiation at a temperature at which water in the mixture is frozen.

9 Claims, No Drawings

IMMOBILIZATION OF ENZYMES OR BACTERIAL CELLS

CROSS-REFERENCE TO RELATED APPLICATION

The present application is a continuation-in-part of U.S. application Ser. No. 523,162, filed Nov. 12, 1974, and now abandoned.

BACKGROUND OF THE INVENTION

This invention relates to novel polymer composition having fixed bacterial cells and/or fixed enzymes, in which the enzyme or cells are dispersed within the polymer and to a process for producing the same.

Recently the enzyme industry has become important and has made remarkable progress in producing medicine and food by utilizing enzyme or cells to carry out reactions.

In the prior art the enzyme reaction was effected by using enzyme solution. In this case, however, after the reaction is completed, the enzyme solution employed in the reaction cannot be reused, because the used enzyme solution contains the resulting reaction product. Therefore, since the enzyme solution employed in the one reaction must be removed from the reaction system, the batch system must be used for the enzyme reaction. In other words, in an enzyme reaction using enzyme solution, the maximum effectiveness of the enzyme is not obtained.

In recent years, attempts have been made to prepare an enzyme-polymer composition which could be reused in the enzyme reaction many times. One such composition comprises dispersing the enzyme into a polymeric material or bonding the enzyme to the polymer, and then forming a porous gel or particles from the resulting dispersion. In other words, the research has been directed toward fixing an enzyme or making the enzyme insoluble.

For example, one process for fixing an enzyme comprises dissolving a water-soluble monomer, such as acrylamide, in an aqueous solution of enzyme, and then simultaneously polymerizing and crosslinking the monomer to form a gel comprising the resulting polymer and the enzyme, and evaporating water from the gel to form a porous material.

Another process for fixing an enzyme comprises dissolving a water-soluble polyvinyl alcohol in an enzyme solution and then effecting crosslinking thereof by a known process and evaporating water from the solution to form a porous material. In these processes, the enzyme is dispersed in a water-soluble polymer, whereby the enzyme is fixed or is made insoluble to some extent.

However, the prior processes have the following disadvantages. In these processes, since the monomer to be polymerized as well as the polymer thus formed are water soluble, the polymer composition obtained by the polymerization is a clear gel in which the enzyme and the polymer are dissolved in water. In order to obtain the porous material necessary for carrying out the enzyme reaction from the gel, the large amount of water contained in the gel must be removed. In addition, the porous material obtained by removing water is large lumps comprising a firm, rigid and porous gel, A satisfactory enzyme reaction cannot be effected by using a lumpy gel, because the total surface area of the large lumps is small. Therefore, in order to carry out the enzyme reaction effectively, the large lumps of gel must be ground or pulverized to increase the surface area of the porous material. However, the removal of water from the gel and grinding the large lumps of gel require much time and much labor. In addition, since the polyacrylamide is noxious, a porous material containing the polyacrylamide and the enzyme is not usable in the food industry.

The present invention eliminates these advantages. The present invention provides a porous material obtained by polymerizing a specific monomer containing an enzyme or bacterial cells.

SUMMARY OF THE INVENTION

Therefore, one object of this invention is to provide a process for producing a porous material comprising specific polymer and an enzyme or bacterial cells, in which the procedure for fixing the enzyme or bacterial cell is simplified and improved.

Another object of the present invention is to provide porous polymer composition comprising an enzyme or bacterial cells and a specific water-insoluble polymer, in which the enzyme or bacterial cells are fixed or are made insoluble.

Another object of the present invention is to provide process for producing a porous polymer material comprising an enzyme or bacterial cells and polymer, in which the process is simplified and made more economical.

DETAILED DESCRIPTION OF THE INVENTION

This invention relates to a process for producing a porous polymer composition containing solid enzyme or bacterial cells, characterized by mixing one or more polymerizable monomers selected from the group consisting of hydroxyethyl methacrylate, hydroxyethyl acrylate, hydroxypropyl methacrylate and hydroxypropyl acrylate with an aqueous solution of enzyme or a dispersion of bacterial cells in water, and then polymerizing and/or copolymerizing the monomers contained in the mixture by means of an ionizing radiation, thereby depositing the porous polymer material within which the enzyme or cells are dispersed, the irradiation being conducted at a temperature of which the water in the system is frozen.

This invention relates to polymer composition containing fixed enzyme and/or bacterial cells, characterized in that the polymer and the enzyme or bacterial cells are dispersed within the polymer, said polymer being prepared by polymerizing and/or copolymerizing one or more monomers selected from the group consisting of hydroxyethyl methacrylate, hydroxyethyl acrylate, hydroxypropyl methacrylate and hydroxypropyl acrylate.

One enzyme or one kind of bacterial cells may be fixed according to the present invention. Two or more enzymes or two or more kinds of cells may also be fixed. Furthermore, a mixture of enzyme and cells may be fixed.

By "enzyme reaction" we mean a reaction in which an enzyme or cells are employed as a catalyst, an initiator or a reactant.

By the fixation of enzyme or cells we mean that the enzyme or cells are held by the polymer so that enzyme or cells may be employed in the enzyme reaction many times.

The polymer composition having fixed enzyme or fixed cells is a porous, solid material.

The monomers which are employed in this invention are easily miscible with water and are dissolved in the aqueous enzyme solution or in the dispersion of bacterial cells in water over a wide range of concentration. That is, the monomers are dissolved in water or buffer solution which is a dispersing agent for the bacterial cells, thereby uniformly dispersing the cells in the water or buffer solution.

The monomers employed in the present invention have advantages over the acrylamide employed in the prior art in the following points:

(a) The polyacrylamide employed in the prior art is water soluble, whereas the polymers obtained by polymerizing the monomers employed in the present invention are water insoluble and are deposited in the system as the polymerization proceeds.

(b) Upon completion of polymerization, the polymer made from the monomers in the present invention is in the solid state, either in the form of very porous gel or of porous powder. On the other hand, since polyacrylamide is water soluble, it does not pass to a porous solid state only by polymerizing acrylamide monomer.

(c) When the polymer of the present invention is deposited, the polymer closely intervenes with the enzyme or cells to form the deposit of polymer. In addition, since the polymer employed in the present invention tends to crosslink as the polymerization proceeds, the enzyme or cells can be closely held by the polymer.

(d) Polyacrylamide is noxious, whereby the polymer of the present invention is not noxious.

(e) The monomers employed in the present invention are polymerized at a lower dose of an ionizing radiation than polyamide is. Therefore, according to the present invention, the enzyme and cells can be fixed without their deactivation.

Upon completion of the polymerization, the polymer composition containing the enzyme or cells has already become porous. Therefore, this invention does not require the steps of washing, purifying, drying, grinding, etc. The enzyme or cells-polymer composition incorporating the enzyme or cell obtained by polymerizing the monomer in the present invention is usable in the enzyme reaction, as it is.

Even where finely divided powder catalyst is to be used in the enzyme reaction, in many cases, the finely divided powder composed of the enzyme or cells-polymer composition may be prepared only by polymerizing the monomer according to the present invention.

If the finely divided powder cannot be prepared only by polymerizing the monomer, the resulting composition can be easily pulverized by drying it, because the composition is very porous and has large void space. In this case, since water is liberated or removed from the molecules of the enzyme composition, the composition dries quickly, and the composition can be ground after only air drying.

Since the enzyme or cells-polymer composition prepared according to the present invention has large porosity and is easily reduced to a fine powder, diffusion of the reactants in the enzyme reaction is easy. As a result, a high reaction rate can be achieved. In other words, the enzyme or cells-polymer composition prepared according to the present invention is more porous and has more surface area than the enzyme-polymer composition comprising the enzyme and water soluble polymer prepared according to the prior art, so the enzyme reaction activity of the former is greater than that of the latter.

The mixture of the monomer and the enzyme or bacterial cells is polymerized by irradiating the system with an ionizing radiation. Since the enzyme tends to be deactivated at an elevated temperature, the polymerization of the monomers in the polymerization system containing the enzyme is effected at as low temperature as possible in order to prevent the deactivation of the enzyme or cells. The polymerization can be effected by means of irradiation at a temperature of which the water in the system is frozen.

Polymerization can also be effected at said temperature by irradiating the monomer with an ionizing radiation. The ionizing radiation includes $\alpha$-rays, $\beta$-rays, electron, X-rays, $\gamma$-rays, neutron and mixed rays emitted from nuclear reactor. In case of irradiation, the polymerization can be effected at such a low temperature that liquid nitrogen may be present in the polymerization system. Since the monomer employed in the present invention can be polymerized at a low total dose, the enzyme or cell present in the polymerization system is not deactivated.

This invention also relates to a process for producing porous enzyme or bacterial cells-polymer composition, characterized by mixing (a) one or more polymerizable monomers selected from the group consisting of hydroxyethyl methacrylate, hydroxyethyl acrylate, hydroxypropyl methacrylate and hydroxypropyl acrylate (b) one or more monomers other than said monomers in the amount of less than 40% by weight preferably less than 20% by weight on the basis of the total monomer and (c) an aqueous solution of enzyme or a dispersion of cells in water, and then polymerizing the monomers contained in the mixture by means of an ionizing radiation, thereby depositing the porous polymer composition in which the enzyme or cells are dispersed within the polymer. The polymerization temperature is the one of which the water in the system is frozen.

This invention also relates to porous polymer composition having enzyme or cells, characterized in that said polymer is prepared by polymerizing and/or copolymerizing one or more monomers selected from the group consisting of hydroxyethyl methacrylate, hydroxyethyl acrylate, hydroxypropyl methacrylate and hydroxypropyl acrylate and one or more monomers other than said monomers in the amount of less than 40% by weight on the basis of the total monomers, or mixture of said copolymer and the polymer, and in the composition the enzyme or cells are dispersed within the polymer. In this case, the monomers other than hydroxyethyl methacrylate, hydroxyethyl acrylate, hydroxypropyl methacrylate and hydroxypropyl acrylate are employed in the amount of less than 40% by weight, preferably less than 20% by weight on the basis of the total monomer.

The purpose of adding other monomers to the polymerization system is to increase the rate of precipitation of the polymer, to promote separation of water from the system and promote codeposition of the enzyme or cells and the polymer to make the polymer more porous when the polymer deposits, to make the particles of the polymer finer when the polymer deposits, to effectively and simply prepare the enzyme or cells-polymer composition having great activity, to increase the crosslinking property of the polymer, to increase stability of holding or fixing the enzyme or bacterial cell in the polymer, and to improve the properties of the resulting enzyme or cells-polymer composition, such as its mechanical strength, its chemical resistance and its thermal stability.

These monomers include ethylene glycol dimethacrylate, ethylene glycol diacrylate, propylene glycol dimethacrylate propylene glycol diacrylate, butanediol dimethacrylate, butanediol diacrylate, pentanediol dimethacrylate, pentanediol diacrylate, hexanediol dimethacrylate, hexanediol diacrylate, triethyleneglycol dimethacrylate, triethyleneglycol diacrylate, polyethyleneglycol dimethacrylate, polyethyleneglycol diacrylate, neopentylglycol dimethacrylate, neopentylglycol diacrylate, polypropyleneglycol dimethacrylate, polypropyleneglycol diacrylate, trimethylolpropane trimethacrylate, trimethylolpropane triacrylate, ethyl methacrylate, methyl methacrylate, butyl methacrylate, isobutyl methacrylate, 2-ethylhexyl methacrylate, cyclohexyl methacrylate, furfuryl methacrylate, benzyl methacrylate, glycidyl methacrylate, stearyl methacrylate, octyl methacrylate, ethyl acrylate, methyl acrylate, butyl acrylate, glycidyl acrylate, vinyl acetate, vinyl propionate, butanediol monomethacrylate, butanediol monoacrylate, pentanediol monomethacrylate, pentanediol monoacrylate, hexanediol monomethacrylate, hexanediol monoacrylate, nonanediol monomethacrylate, nonanediol monoacrylate, vinyl stearate, vinyl palmitianate, vinyl pyrrolidone, acrylic acid, methacrylic acid and metal salts thereof.

When two or more monomers selected from the group consisting of hydroxyethyl methacrylate, hydroxyethyl acrylate, hydroxypropyl methacrylate and hydroxypropyl acrylate are used, or when at least one said monomer and one or more monomers other than said monomers are used, monomers which are more reactive are first polymerized or copolymerized, and then monomers which are less reactive are polymerized. Therefore, in case of using two or more monomers, the polymer composition fixing the enzyme and cells may be composed of a mixture of polymer and copolymer.

The present process is applied to a variety of enzymes and bacterial cells to fix the enzyme(s) and cells or to make them insoluble thereby keeping the activity of the enzyme and cells. In preparing the polymer composition, the ratio of the enzyme(s) or cells to the monomer is not critical.

The enzymes which are fixed or are made insoluble by the present invention include urease, alcohol dehydrogenase, lactic dehydrogenase, malic dehydrogenase, glycose oxidase, diamine oxidase, glycose oxidase-catalase, D-amino acid oxidase, liposidase, uricase, ribonuclease, hexokinase, lipase, alkaline phosphatase, acidic phosphatase, nucleoedase, deoxyribonuclease, α-amylase, β-amylase, glucoamylase, glycoseisomerase, cellulase, hemicellulase, β-glucosidase, invertase, anthocyanase, narindinase, hesperidinase, β-glucuronidase, hyaluronidase, alkaline protease, semialkaline protease, acidic protease, thermorairin, collagenase, pepsin-pepsinagen, aminopeptidase, rennin, trypsintrypsinogen, chymotrypsinogen, elastase, enterodinase, acylase, arginase, L-glutamic acid decarboxylase, L-lysine decarboxylase, and papain.

The bacterial cells which are fixed or are made insoluble by the present invention include cells containing the above mentioned enzymes, Aerobacter-aerogenes, Azotobactervinelandii, Bacillus-subtilis, Escherrichia-coli and Micrococcus-lysodeikticus. Other enzymes and bacterial cells can be fixed or made insoluble according to the present invention.

In carrying out the present invention, polymerizing the monomer(s) and making the resulting polymer porous are simultaneously effected to obtain the powdered enzyme or cells-polymer composition in which the enzyme or cells are dispersed within the polymer. The present invention does not need a purifying step, a drying step (a step for making the gel porous) and a grinding step. According to the present invention, the procedure for fixing the enzyme and bacterial cells or making them insoluble is simple in comparison with the prior art, and therefore, the present invention is efficient. Furthermore, the enzyme or cells-polymer composition according to the present invention is obtained in the form of finely divided particles and has large surface area contributing to the enzyme reaction, and has a large void space in the inner part of the composition. Consequently, the method of the present invention is more effective for fixing the enzyme than the prior art methods.

The invention is further illustrated, but in no way limited, by the following Examples.

EXAMPLE 1

25 mg of urease was dissolved in 50 cc of a buffer solution, and 10 cc of hydroxyethyl methacrylate was added to the mixture, and was uniformly mixed.

The resulting solution was irradiated with γ-ray from cobalt 60 at a dose rate of $5\times10^5$ R/hr for an hour at a temperature of 0° C. to form white polymer precipitate. The yield of polymerization is 99.8%.

Without effecting purifying and drying steps, the resulting polymer was added to a mixture solution of 20 cc of 0.02 M phosphate buffer solution and 20 cc of 0.02 M urea solution. A conversion of the urea to ammonia and carbon dioxide was effected at a temperature of 25° C. for 30 minutes. From the resulting mixture, 4 cc of sample was withdrawn. To the sample was added 4 cc of 0.1 N HCl to discontinue the reaction. Titration was effected with 0.05 N NaOH to obtain the activity of the enzyme-polymer composition prepared in this Example.

Control test was effected by following the above experiment except that the enzyme was used in the state of solution. Similarly, the activity of the enzyme solution was obtained.

The ratio of the activity of the enzyme-polymer composition of the present invention obtained in Example 1 to the activity of the enzyme solution (hereinunder referred to as the degree of maintaining the activity) was 27.2%.

A second experiment was effected by using the same enzyme-polymer composition that was employed in the first experiment. The procedure used in the second experiment was the same as that used in the first experiment. The degree of maintaining the activity in the second experiment was 25.9%. Similarly, third and fourth experiments were effected by using the same composition that was employed in the second and third experiments. The results are given in the following.

Table 1

|  | First experiment | Second experiment | Third experiment | Fourth experiment |
|---|---|---|---|---|
| Degree of maintaining activity (%) | 27.2 | 25.9 | 25.5 | 25.2 |

The activity of the enzyme-polymer composition is on the order of about 25% per 100% of the activity of the enzyme solution. However, the enzyme solution is usable for the enzyme reaction only one time, whereas the enzyme-polymer composition of the present invention is usable for the reaction several or more times. Therefore, the enzyme-polymer composition of the present invention is effectively utilized.

EXAMPLE 2

Example 1 was repeated except that hydroxyethyl methacrylate in the amount as shown in Table 2 was used. That is, four enzyme-polymer composition were prepared by using 20 cc, 30 cc, 40 cc and 50 cc of hydroxyethyl methacrylate, respectively, and four experiments were carried out using the same composition that was employed in the first experiment, the same as Example 1. The degree of maintaining the activity of the polymer (the ratio of activity of the enzyme-polymer article prepared according to Example 2 to the activity of the enzyme solution) was calculated and is shown in Table 2.

Table 2

| Amount of hydroxyethyl methacrylate added | Degree of maintaining activity % | | | |
|---|---|---|---|---|
| | First experiment | Second experiment | Third experiment | Fourth experiment |
| 20 cc | 39.5 | 36.2 | 36.0 | 35.8 |
| 30 | 51.6 | 51.1 | 51.1 | 50.5 |
| 40 | 60.3 | 59.8 | 59.3 | 58.3 |
| 50 | 69.9 | 69.7 | 69.5 | 69.5 |

EXAMPLE 3

25 mg of glucose isomerase was dissolved in 50 cc of a buffer solution, and 10 cc of hydroxyethyl acrylate was added to the solution and mixed to get a uniform mixture. The resulting solution was irradiated with γ-ray from cobalt 60 at a dose rate of $1 \times 10^5$ R/hr at a total dose of $2 \times 10^5$ R at a temperature of $-30°$ C. to deposit white polymer.

Without effecting purifying and drying steps, the resulting polymer was added to 20 cc of a glucose solution dissolved in a phosphate buffer solution containing $Mg^{++}$. The glucose were converted to fructose at a temperature of 70° C. for an hour. 4 cc of sample was withdrawn from the resulting solution, and the sample was color-developed through cysteine-carbazole reaction. The amount of furctose thus formed was determined from color comparison of 560 mu, whereby the activity of the enzyme-polymer composition prepared according to Example 3 was calculated. Second, third and fourth experiments were effected using the same composition that was employed in the first experiment, the same as in Example 1.

The degree of maintaining the activity of the polymer (the ratio of activity of the enzyme-polymer composition prepared by Example 3 to the activity of the enzyme, solution) was calculated and shown in Table 3.

Table 3

| | First experiment | Second experiment | Third experiment | Fourth experiment |
|---|---|---|---|---|
| Degree of maintaining activity (%) | 58.5 | 55.7 | 55.4 | 55.5 |

EXAMPLE 4

25 mg of α-amylase dissolved in 50 cc of a buffer solution, and a mixture of 10 cc of hydroxyethyl methacrylate and 5 cc of acrylic acid was added to the solution and mixed to get a uniform solution. The resulting solution was irradiated with γ-ray from cobalt 60 at a dose rate of $5 \times 10^4$ R/hr at a total dose of $1 \times 10^5$ R at a temperature of $-20°$ C. to deposit white polymer.

Without effecting purifying and drying steps, the resulting polymer was added to 50 cc of a 1% solution of potato starch paste. The starch was converted to maltose at a temperature of 40° C. for 20 minutes. The activity of the polymer prepared by this Example was calculated determining the reducing action of the starch through Somogyi's method.

Second, third and fourth experiments were carried out using the same composition that was employed in the first experiment, the same as in Example 1.

The degree of maintaining the activity of the polymer (the ratio of activity of the enzyme-polymer composition prepared by this Example to the activity of the enzyme, α-amylase solution) was calculated and is shown in Table 4.

Table 4

| | First experiment | Second experiment | Third experiment | Fourth experiment |
|---|---|---|---|---|
| Degree of maintaining activity (%) | 77.5 | 75.1 | 74.2 | 73.6 |

REFERENCE EXAMPLE 25 mg of urease was dissolved in 50 cc of a buffer solution and 10 g acrylamide was added to the solution and was mixed to get a uniform solution. The resulting solution was irradiated with γ-rays from cobalt 60 at a dose rate of $5 \times 10^5$ R/hr at a total dose for 1 hour at a temperature of 0° C. to form colorless, clear polymer in a gel state. The rate of polymerization was 99.9%.

Since the polymer has no void spaces, it does not have the activity for carrying out the enzyme reaction. The polymer was dried at a room temperature for 240 hours to evaporate water from the polymer, and was ground by using rolls. The ground polymer was added to a mixture of 20 cc of 0.02 M phosphate buffer solution and 20 cc of 0.02 M aqueous solution of urea. The urea was converted to ammonia and $CO_2$ at a temperature of 25° C. for 30 minutes. 4 cc of sample was withdrawn from the resulting solution. To the sample was added 4 cc of 0.1 N HCl to discontinue the reaction. Titration was effected with 0.05 N NaOH to obtain the enzyme-polymer composition prepared in this Example.

Second, third and fourth experiments were effected by using the same composition that was employed in the first experiment, the same as in Example 1. The degree of maintaining activity of the polymer (the ratio of activity of the enzyme-polymer composition prepared by this Example to the activity of the enzyme solution) was calculated and is shown in Table 5.

Table 5

| | First experiment | Second experiment | Third experiment | Fourth experiment |
|---|---|---|---|---|
| Degree of maintaining | 4.4 | 3.9 | 3.6 | 3.5 |

Table 5-continued

| | First experiment | Second experiment | Third experiment | Fourth experiment |
|---|---|---|---|---|
| activity (%) | | | | |

What is claimed is:

1. A process for producing a porous, water-insoluble polymer composition containing fixed enzyme and/or fixed bacterial cells which comprises mixing an aqueous enzyme solution or an aqueous dispersion of bacterial cells with one or more monomers selected from the group consisting of hydroxyethyl methacrylate, hydroxyethyl acrylate, hydroxypropyl methacrylate and hydroxypropyl acrylate, and then polymerizing and/or copolymerizing the monomer(s) contained in the mixture by means of an ionizing radiation, thereby depositing the polymer containing enzyme and/or cells from water, the irradiation being conducted at a temperature at which the water in the mixture is frozen.

2. A process for producing a porous, water-insoluble polymer composition containing fixed enzymes and/or fixed bacterial cells which comprises mixing (a) an aqueous enzyme solution or an aqueous dispersion of bacterial cells, (b) one or more monomers selected from the group consisting of hydroxyethyl methacrylate, hydroxyethyl acrylate, hydroxypropyl methacrylate and hydroxypropyl acrylate and (c) one or more monomers other than said monomers in the amount of less than 40% by weight on the basis of the total monomers, and then polymerizing and/or copolymerizing the monomers contained in the mixture by means of an ionizing radiation, thereby depositing the polymer containing enzyme and/or cells from water, the irradiation being conducted at a temperature at which the water in the mixture is frozen.

3. The process defined in claim 2, wherein the monomer other than hydroxyethyl methacrylate, hydroxyethyl acrylate, hydroxypropyl methacrylate and hydroxypropyl acrylate is used in the amount of less than 20% by weight on the basis of the total monomers.

4. Porous, water insoluble polymer composition containing fixed enzyme and/or fixed bacterial cells, characterized in that in said composition the enzyme or cells are dispersed within the polymer, said polymer being prepared by polymerizing and/or copolymerizing one or more monomers selected from the group consisting of hydroxyethyl methacrylate, hydroxyethyl acrylate, hydroxypropyl methacrylate and hydroxypropyl acrylate in accordance with the process of claim 1.

5. The composition defined in claim 4, wherein the polymer is composed of one or more polymers.

6. Porous, water insoluble polymer composition containing fixed enzyme and/or fixed bacterial cells, characterized in that in said composition, the enzyme or cells are dispersed within the polymer, said polymer being prepared by polymerizing and/or copolymerizing one or more monomers selected from the group consisting of hydroxyethyl methacrylate, hydroxyethyl acrylate, hydroxypropyl methacrylate and hydroxypropyl acrylate and one or more monomers other than said monomers in the amount of less than 40% by weight on the basis of the total monomers in accordance with the process of claim 2.

7. The composition defined in claim 6, wherein the monomer other than hydroxyethyl methacrylate, hydroxyethyl acrylate, hydroxypropyl methacrylate and hydroxypropyl acrylate is used in the amount of less than 20% by weight on the basis of the total monomers.

8. The process in accordance with claim 2, wherein the monomer or monomers other than hydroxyethyl methacrylate, hydroxyethyl acrylate, hydroxypropyl methacrylate and hydroxypropyl acrylate are one or more monomers selected from the group consisting of ethylene glycol dimethacrylate, ethylene glycol diacrylate, propylene glycol dimethacrylate, propylene glycol diacrylate, butanediol dimethacrylate, butanediol diacrylate, pentanediol dimethacrylate, pentanediol diacrylate, hexanediol dimethacrylate, hexanediol diacrylate, triethyleneglycol dimethacrylate, triethyleneglycol diacrylate, polyethyleneglycol dimethacrylate, polyethyleneglycol diacrylate, neopentylglycol dimethacrylate, neopentylglycol diacrylate, polypropyleneglycol dimethacrylate, polypropyleneglycol diacrylate, trimethylolpropane trimethacrylate, trimethylolpropane triacrylate, ethyl methacrylate, methyl methacrylate, butyl methacrylate, isobutyl methacrylate, 2-ethylhexyl methacrylate, cyclohexyl methacrylate, furfuryl methacrylate, benzyl methacrylate, glycidyl methacrylate, stearyl methacrylate, octyl methacrylate, ethyl acrylate, methyl acrylate, butyl acrylate, glycidyl acrylate, vinyl acetate, vinyl propionate, butanediol monomethacrylate, butanediol monoacrylate, pentanediol monomethacrylate, pentanediol monoacrylate, hexanediol monomethacrylate, hexanediol monoacrylate, nonanediol monomethacrylate, nonanediol monoacrylate, vinyl stearate, vinyl palmitianate, vinyl pyrrolidone, acrylic acid, methacrylic acid and metal salts thereof.

9. The composition in accordance with claim 6, wherein the monomer or monomers other than hydroxyethyl methacrylate, hydroxyethyl acrylate, hydroxypropyl methacrylate and hydroxypropyl acrylate are one or more monomers selected from the group consisting of ethylene glycol dimethacrylate, ethylene glycol diacrylate, propylene glycol dimethacrylate, propylene glycol diacrylate, butanediol dimethacrylate, butanediol diacrylate, pentanediol dimethacrylate, pentanediol diacrylate, hexanediol dimethacrylate, hexanediol diacrylate, triethyleneglycol dimethacrylate, triethyleneglycol diacrylate, polyethyleneglycol dimethacrylate, polyethyleneglycol diacrylate, neopentylglycol dimethacrylate, neopentylglycol diacrylate, polypropyleneglycol dimethacrylate, polypropyleneglycol diacrylate, trimethylolpropane trimethacrylate, trimethylolpropane triacrylate, ethyl methacrylate, methyl methacrylate, butyl methacrylate, isobutyl methacrylate, 2-ethylhexyl methacrylate, cyclohexyl methacrylate, furfuryl methacrylate, benzyl methacrylate, glycidyl methacrylate, stearyl methacrylate, octyl methacrylate, ethyl acrylate, methyl acrylate, butyl acrylate, glycidyl acrylate, vinyl acetate, vinyl propionate, butanediol monomethacrylate, butanediol monoacrylate, pentanediol monomethacrylate, pentanediol monoacrylate, hexanediol monomethacrylate, hexanediol monoacrylate, nonanediol monomethacrylate, nonanediol monoacrylate, vinyl stearate, vinyl palmitianate, vinyl pyrrolidone, acrylic acid, methacrylic acid and metal salts thereof.

* * * * *